United States Patent [19]

Jaeger et al.

[11] Patent Number: 5,627,179
[45] Date of Patent: May 6, 1997

[54] MAGNESIUM SALT OF 3-ISOPROPYL-2, 1, 3-BENZOTHIADIAZIN -4-ONE 2,2-DIOXIDE, ITS PREPARATION AND ITS USE FOR CONTROLLING UNDESIRABLE PLANT GROWTH

[75] Inventors: Karl-Friedrich Jaeger, Limburgerhof; Adolf Parg, Bad Durkheim; Alfons Durein, Roemerberg, all of Germany

[73] Assignee: Basf Aktiengesellschaft, Ludwigshafen, Germany

[21] Appl. No.: 537,909

[22] PCT Filed: May 2, 1994

[86] PCT No.: PCT/EP94/01391

§ 371 Date: Oct. 26, 1995

§ 102(e) Date: Oct. 26, 1995

[87] PCT Pub. No.: WO94/26727

PCT Pub. Date: Nov. 24, 1994

[30] Foreign Application Priority Data

May 12, 1993 [DE] Germany ............... 43 15 878.1

[51] Int. Cl.$^6$ ............... C07D 285/16; A01N 25/08
[52] U.S. Cl. ............... 514/222.8; 544/11
[58] Field of Search ............... 544/11; 514/222.8

[56] References Cited

U.S. PATENT DOCUMENTS

| | | | |
|---|---|---|---|
| 3,849,104 | 11/1974 | Daniel et al. | 71/65 |
| 3,989,506 | 11/1976 | Fischer | 71/91 |
| 3,999,973 | 12/1976 | Templeton | 71/79 |
| 4,208,514 | 6/1980 | McKendry et al. | 544/11 |
| 4,419,120 | 12/1983 | Walker et al. | 71/79 |
| 4,775,405 | 10/1988 | Caulder et al. | 71/79 |
| 4,988,818 | 1/1991 | Lauer et al. | 548/267.4 |
| 5,266,553 | 11/1993 | Champion et al. | 504/206 |

FOREIGN PATENT DOCUMENTS

| | | | |
|---|---|---|---|
| 1405638 | 9/1975 | United Kingdom | A01N 9/14 |
| 1417279 | 12/1975 | United Kingdom | A01N 9/02 |
| 2007978 | 5/1979 | United Kingdom | A01N 9/02 |

OTHER PUBLICATIONS

Shullgin V.F. et al CA 115:92230 U. LH. Obshch. Khim, 1991, 61(2), 456–9 (Russ).

Primary Examiner—Mukund J. Shah
Assistant Examiner—Sabiha N. Qazi
Attorney, Agent, or Firm—Keil & Weinkauf

[57] ABSTRACT

Solid, non-hygroscopic magnesium salt of 3-isopropyl-2,1,3-benzothiadiazin-4-ones 2,2-dioxide (I), processes for its preparation, solid formulations, in particular granules, which contain this salt, and the use thereof for controlling undesirable plant growth.

12 Claims, No Drawings

MAGNESIUM SALT OF 3-ISOPROPYL-2, 1, 3-BENZOTHIADIAZIN -4-ONE 2,2-DIOXIDE, ITS PREPARATION AND ITS USE FOR CONTROLLING UNDESIRABLE PLANT GROWTH

This application is a 35 USC371 National stage of international application PCT/FP94/01391, filed May 2, 1994.

The present invention relates to a solid, nonhygroscopic magnesium salt of 3-isopropyl-2,1,3-benzothiadiazin-4-one 2,2-dioxide I.

The present invention furthermore relates to solid formulations of this salt, processes for the preparation of this salt, agents, in particular powders, granules and water-soluble or water-dispersible foil bags which contain this salt, and the use thereof for controlling undesirable plant growth.

The literature discloses benzothiadiazin-4-one 2,2-dioxides and salts thereof as herbicides (DE-A 15 42 836, DE-A 21 64 459 and DE-A 22 17 722). With regard to the use of salts, DE-A 15 42 836, DE-A 21 64 459 and DE-A 22 17 722 also mention generally alkaline earth metal salts as application forms, the potassium salts being singled out. However, these publications do not mention any special properties, in particular of the magnesium salts.

The use of water-soluble or water-dispersible foil bags for the handling of crop protection agents in a manner which is safe for the user is disclosed in, for example, EP-A 449 773 and EP-A 493 553.

3-Isopropyl-2,1,3-benzothiadiazin-4-one 2,2-dioxide (INN name: bentazone) is usually formulated as a highly concentrated aqueous solution, the sodium salt or the diethanolammonium salt, owing to its more advantageous dissolution properties, being used in preference to the acid. For use, these bentazone solutions are diluted with water and applied by spraying.

A solid formulation (for example a granular formulation) is desirable for simple and safe use of bentazone formulations and for easy disposal of the packaging.

Dust-free granular formulations can be easily and safely used. Compared with the liquid formulations used to date, there are advantages in the form of reduced use of packaging material and safe storage. At low storage temperatures, undesirable crystallization may occur in the case of liquid products.

Furthermore, solid formulations can be packed in water-soluble or water-dispersible foil bags. When used, the foil bag containing the product is dissolved or dispersed in the spray tank. Packaging contaminated with product residues is thus avoided.

Sodium bentazone, calcium bentazone and potassium bentazone have the disadvantage of being very hygroscopic. In the case of solid formulations, this results in the product gradually agglomerating or even coalescing merely under the influence of atmospheric humidity and hence being no longer capable of being directly metered. Even the introduction of these compounds into water-soluble foil bags has no advantage since the films are dehydrated owing to the inter-action of the hygroscopic active ingredients on the one hand and the films on the other hand. The films therefore become brittle, i.e. a long shelf life is no longer guaranteed. The diethanolamine salt of bentazone cannot be dried to give a solid product (melting point <20° C.).

It is an object of the present invention to provide a nonhygroscopic solid formulation of the active ingredient bentazone, which formulation has a long shelf life.

We have found that this object is achieved by the salt stated at the outset, solid formulations of this salt, processes for its preparation, agents, in particular powders and granules, and water-soluble foil bags which contain this salt and the use thereof for controlling undesirable plant growth.

For the purposes of the present invention, the term nonhygroscopic is to be understood as meaning that, in equilibrium with humid air at 20° C. and a relative humidity of 50%, the salt I does not agglomerate but remains free-flowing and hence meterable. Furthermore, the salt I does not dehydrate the water-soluble films, i.e. the foil bags remain flexible and hence stable even on prolonged storage.

The preparation of 3-isopropyl-2,1,3-benzothiadiazin-4-one 2,2-dioxide is known from the literature cited at the outset.

The magnesium salt is obtained by treating or extracting 3-isopropyl-2,1,3-benzothiadiazin-4-one 2,2-dioxide (II) in aqueous solution with a magnesium compound and then isolating and drying the solid in a conventional manner.

The reaction temperature is not critical for the salt formation and only has an effect on the solubility of the starting materials used and hence on the reaction concentration. Accordingly, the salt formation can be carried out at from 10° C. to the boiling point of the solution.

The magnesium compounds usually used are hydroxides, oxides, carbonates and bicarbonates.

These magnesium compounds are usually used in equimolar amounts, based on (II). In order to complete the reaction, it may be advantageous to use the inorganic compounds in excess. This excess should in turn be kept small, owing to the undesirable pollution of the resulting waste waters containing salts. Thus, the excess usually need not exceed 10 mol %.

II may be reacted directly in aqueous solution with the abovementioned salts, or II is extracted from an organic solution into the aqueous phase which contains the magnesium salts.

It is also possible to react an aqueous or organic solution of an ammonium or alkali metal salt of the compound II with a magnesium salt.

The solid salt may be isolated in a conventional manner by crystallization and/or by drying of the aqueous solution of I by a generally customary method. Examples are fluidized-bed drying, spray drying or drying under reduced pressure.

In order to prepare granules, drying is advantageously carried out by the fluidized-bed method or by agglomeration of a powder of I which is prepared by spray drying or drying under reduced pressure.

The granules thus obtained usually consist of from 20 to 100% of magnesium salt I. The particle size of these granules is in general from 200 to 3000 μm. The dust fraction of the granules is small. The dust content of a 30 g sample is less than 20 mg (CI-PAC MT 171: Dustiness of Granular Formulations), ensuring a high degree of safety for the user. The bulk density of such granules is 400–800 g/l.

It is also possible to introduce the magnesium salt of 3-isopropyl-2,1,3-benzothiadiazin-4-one 2,2-dioxide, whether it is crystalline, in the form of a powder or as granules, into water-soluble or water-dispersible foil bags and thus to ensure safe handling by the users and to avoid contaminated packaging after use.

The filled foil bags usually contain from 0.1 to 10, preferably from 0.5 to 5, kg of active ingredient (I). They are usually completely filled with the active ingredient, an active ingredient formulation or an active ingredient mixture. However, it is also possible for the foil bags to have a larger volume, so that additives and/or other active ingredients may be added. The foil bags are solid and flexible at conventional temperatures and humidities and are welded at least along one side. The thickness of the films is from 20 to 100, preferably from 30 to 60, micron. The water content of the polymeric films may be up to 20%.

Such foil bags as such are disclosed, for example, in EP-A 449 773 or EP-A 493 553. The polymers used for their production are, for example, polymeric polyvinyl alcohols, preferably polyvinyl alcohol polymers with polyvalent alcohols, polymeric polyvinyl alcohols, preferably polyvinyl alcohol polymers with polyvalent alcohols [sic], methylcellulose, ethylene oxide copolymers, polymers of vinylpyrrolidone or vinyl acetate, gelatine, carboxymethylcellulose, dextrose, hydroxyethylcellulose or methylcellulose combined with polyvalent alcohols, such as ethylene glycol, propylene glycol, glycerol, sorbitol and others.

For the protection of the foil bags, it may be advantageous to pack them in larger containers or packets. Suitable packaging materials are cheap materials, such as plastic, paper, cardboard or aluminum. Such packaging is safe from the point of view of environmental pollution and disposal since they do not come into contact with the crop protection active ingredients. It is also possible to reuse such packaging, thus making it possible to further reduce the raw material requirement and hence the environmental pollution.

The granules obtained as above or the filled foil bags may contain, in addition to the salts I, further conventional additives, for example surfactants, fillers or further crop protection active ingredients.

Suitable surfactants are alkali metal, alkaline earth metal and ammonium salts of aromatic sulfonic acids, for example ligninsulfonic, phenolsulfonic, naphthalenesulfonic and dibutylnaphthalenesulfonic acid, and of fatty acids, alkylsulfonates and alkylarylsulfonates, alkylsulfates, lauryl ether sulfates and fatty alcohol sulfates, as well as salts of sulfated hexa-, hepta- and octadecanols or fatty alcohol glycol ethers, condensates of sulfonated naphthalene and its derivatives with formaldehyde, condensates of naphthalene or of naphthalenesulfonic acids with phenol and formaldehyde, polyoxyethylene octylphenol ether, ethoxylated isooctyl-, octyl- or nonylphenol, alkylphenol polyglycol ether or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate [sic], sorbitol esters, ligninsulfite waste liquors or methylcellulose.

Fillers or solid carriers used are, for example, mineral earths, such as silica gel, silicas, silicates, talc, kaolin, limestone, lime, chalk, bole, loess, clay, dolomite, kieselguhr, calcium sulfate, magnesium sulfate or magnesium oxide, milled plastics and fertilizers, such as ammonium sulfate, ammonium phosphate, ammonium nitrate, ureas and vegetable products, such as grain flour, barkmeal, woodmeal and nutshell meal, cellulosic powders and other solid carriers.

The formulations contain in general from 20 to 100, preferably from 50 to 100%, by weight of the salt I. The magnesium salt I is used in a purity of from 90 to 100%, preferably from 95 to 100% (according to NMR/HPLC/GC spectrum).

The granules described above or the water-soluble or water-dispersible foil bags filled with the salts I may be used by the user to prepare aqueous solutions which are then used, in a manner customary for bentazone or for the corresponding mixture, for controlling undesirable plants.

The aqueous solutions thus obtained may be applied in a conventional manner by the preemergence or postemergence method. If the active ingredients are less well tolerated by certain crops, it is possible to employ, in postemergence use, application methods in which the herbicides are applied with the aid of the sprayers in such a way that the leaves of the sensitive crops are as far as possible not wet while the active ingredients reach the leaves of undesirable plants growing underneath or reach the uncovered soil surface (post-directed, lay-by).

The application rates of active ingredient are from 0.001 to 5.0, preferably from 0.01 to 1.0, kg/ha of salt I, depending on the aim of control, the season, the target plant and stage of growth.

CHEMICAL EXAMPLES

1. Preparation of Magnesium Bentazone 1.a. 2.9 parts of magnesium hydroxide are introduced, while stirring, into a mixture consisting of 24 parts of bentazone in 216 parts of 1,2-dichloroethane and 300 parts of water, and stirring is carried out at 60° C. After about 5 hours, a clear, aqueous phase is obtained. After phase separation, the aqueous phase is evaporated to dryness at 50°–60° C. under reduced pressure. 30.1 parts of magnesium bentazone are obtained.

1.b. The experiment corresponds to Example 1.a., the magnesium hydroxide being replaced by 2.02 parts of magnesium oxide.

1.c. 2.9 parts of magnesium hydroxide are introduced, while stirring, into a suspension of 24 parts of bentazone (II) and 300 parts of water, and stirring is carried out for 2 hours at 50° C. The aqueous solution obtained is evaporated to dryness at 50°–60° C. under reduced pressure. 30 parts of magnesium bentazone are obtained.

2. Examples of Solid Formulation 2.a. Preparation of granules using magnesium bentazone A 40% strength aqueous magnesium bentazone solution is dried in a fluidized-bed spray granulator, the temperature of the drying air being 120° C. The magnesium bentazone solution is sprayed into the fluidized bed, and granular particles are formed by agglomeration and drying. The granules consist of 82% of magnesium bentazone and have a water content of 18%. The mean granule size is 0.5 mm. The granules are dust-free and dissolve rapidly in water. They are non-hygroscopic and remain free-flowing and meterable in humid air.

2.b. Preparation of a powder containing 75% of magnesium bentazone 6 parts of sodium ligminsulfonate [sic] are dissolved, while stirring, in a solution of 30 parts of magnesium bentazone in 70 parts of water. This solution is spray-dried in a spray tower, the temperature of the drying air being 160° C. A powder containing 75% of magnesium bentazone is obtained.

Production of Water-soluble Foil Bags 3.a. 430 g of magnesium bentazone are packed in water-soluble KB film (Aicello Chem. Co., Ltd., Japan) and the film is welded tight.

75 l of water at 10° C. are introduced into a sprayer and circulated by means of a pump. The filled foil bags are placed in the sprayer. At a water temperature of 14° C., the product and film are completely dissolved after 2 minutes.

4. Physical Behavior 4.a. Investigation of the hygroscopicity of the salts 1 g of substance in each case was dried for 48 hours at 50° C. under reduced pressure. The dried samples were stored at 55% and 65% relative humidity and 20° C., and the increase in the weight of the samples after reaching the equilibrium state was measured. The flow properties of the samples and their appearance were also evaluated. Substances which are critical with regard to the hygroscopicity absorbed a great deal of water from the air before reaching the equilibrium state. This led to caking of the substances. The results are listed in the table below.

| Type of salt | rel. humidity | Weight increase in % by weight | Properties after storage |
| --- | --- | --- | --- |
| Sodium salt | 55% | 12.6% | lumpy, caked |
| Potassium salt | 55% | 6.7% | lumpy, caked |
| Calcium salt | 55% | 12.0% | lumpy, caked |
| Magnesium salt | 55% | 2.6% | crystalline, free-flowing |
|  | 65% | 2.9% | crystalline, free-flowing |

4.b. Investigation of the behavior of the salts in the foil bag: 10 g of substance in each case, in the form of granules, were welded into foil bags. The filled foil bags (film: Monosol 8030, manufacturer: Chris Craft Inc., USA) were then stored for 4 weeks at various temperatures in water vapor-impermeable outer packaging. The stability of the films is expressed in terms of the flexibility of the films under mechanical stress. When water is absorbed by the bentazone salt, the film releases corresponding amounts of water and becomes brittle. For example, in the presence of sodium bentazone in a closed container, the film Monosol 8030 loses a large part of the residual moisture present in the film. At room temperature, this decreases from an initial value of 14% to 6% in the equilibrium state. The result is embrittlement of the film and splitting of the bag under mechanical stress, such as transport, impact and load. The results of model experiments are summarized in the table below.

| Type of salt | Temperature | Properties of the foil bag |
| --- | --- | --- |
| Sodium salt | 20° C. | brittle, fragile |
|  | 30° C. | brittle, fragile |
| Magnesium salt | 20° C. | flexible, stable |
|  | 30° C. | flexible, stable |

Use examples (herbicidal activity)

The herbicidal action of the salts I was demonstrated by greenhouse experiments:

The culture vessels used were plastic flower pots containing loamy sand with about 3.0% by weight of humus as substrate. The seeds of the test plants were sown separately according to species.

In the preemergence treatment, the active ingredients distributed in water were applied by means of finely distribution of the [sic] nozzles, directly after sowing. The vessels were lightly irrigated in order to promote germination and growth and were then covered with transparent plastic covers until the plants had started to grow. This covering ensured more uniform germination of the test plants, provided that this has not been adversely affected by the active ingredients.

For the postemergence treatment, the test plants were grown to a height of growth of from 3 to 15 cm, depending on the form of growth, and were then treated with the active ingredients distributed in water. The test plants were either sown and grown in the test vessels in which they were treated, or they were sown separately as seedlings and transplanted into the test vessels a few days before the treatment with the active ingredient formulations.

The application rate for the postemergence treatment was 0.5 kg/ha of a.i. (active ingredient).

The plants were kept at from 10° to 25° C., according to species. The test period extended over from 2 to 4 weeks. During this time, the plants were tended and their reaction to the individual treatments was evaluated.

Evaluation was based on a scale from 0 to 100. 100 means no emergence of the plants or complete destruction of at least the above-ground plants and 0 means no damage or normal course of growth.

The plants used in the greenhouse experiments consisted of the following species:

| Code | Botanical name | German name |
| --- | --- | --- |
| ABUTH | Abutilon theophrasti | Velvetleaf |
| AMARE | Amaranthus retroflexus | Redroot pigweed |
| CHEAL | Chenopodium album | Common lambsquarters |
| GALAP | Galium aparine | Catchweed bedstraw |
| IPOSS | Ipomoea ssp. | Morning glory species |
| POLPE | Polygonum persicaria | Ladysthumb |
| SINAL | Sinapis alba | White mustard |
| SOLNI | Solanum nigrum | Black nightshade |
| STEME | Stellaria media | Common chickweed |
| VERSS | Veronica ssp. | Speedwell species |

The biological action of the magnesium salt (I) in comparison with the known sodium salt of 3-isopropyl-2,1,3-benzothiadiazin-4-one 2,2-dioxide (using the same formulation) is shown in the table below.

|  | Herbicidal action % | |
| --- | --- | --- |
|  | Sodium salt | Magnesium salt |
| ABUTH | 100 | 100 |
| AMARE | 55 | 20 |
| CHEAL | 100 | 100 |
| GALAP | 85 | 85 |
| IPOSS | 60 | 75 |
| POLPE | 100 | 100 |
| SINAL | 100 | 100 |
| SOLNI | 100 | 100 |
| STEME | 100 | 100 |
| VERSS | 20 | 10 |

We claim:
1. A solid, non-hygroscopic magnesium salt of 3-isopropyl-2,1,3-benzothiadiazin-4-one 2,2-dioxide (I).
2. A solid formulation consisting of from 20 to 100% by weight of the magnesium salt I as claimed in claim 1.
3. A process for the preparation of the solid, non-hygroscopic magnesium salt I as claimed in claim 1, wherein 3-isopropyl-2,1,3-benzothiadiazin-4-one 2,2-dioxide (II)

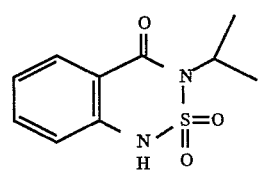

in aqueous solution is treated with an inorganic magnesium compound, and the solid is then isolated and dried in a conventional manner.

4. A process for the preparation of a solid formulation as defined in claim 2, wherein an aqueous solution of a solid, non-hygroscopic magnesium salt of 3-isopropyl-2,1,3-benzothiadiazin-4-one 2,2-dioxide is dried by the spray-drying method, by drying under reduced pressure or by the fluidized-bed method.

5. An agent for controlling undesirable plant growth, comprising an effective amount of the magnesium salt I as claimed in claim 1.

6. A water-soluble or water-dispersible foil bag which comprises a magnesium salt I as claimed in claim 1.

7. A method for controlling undesirable plant growth, wherein the undesirable plants or the area to be kept free from them is or are treated with an effective amount of the magnesium salt I as claimed in claim 1.

8. A method of preparing a water-soluble or a water dispersible foil bag which comprises packing the bag with the magnesium salt I defined in claim 1.

9. A method of preparing a water-soluble or a water-dispersible foil bag which comprises packing the bag with the solid formulation defined in claim 2.

10. A water-soluble or water-dispersible foil bag which comprises the solid formulation defined in claim 2.

11. Active ingredient granules comprising the magnesium salt as defined in claim 1.

12. A method for controlling undesirable plant growth, wherein the undesirable plants or the area to be kept free from them is or are treated with an effective amount of the solid formulation as defined in claim 2.

* * * * *